United States Patent
Oh

(10) Patent No.: US 6,948,933 B2
(45) Date of Patent: Sep. 27, 2005

(54) COMPLEX ROOT CANAL PLUGGING APPARATUS FOR DENTAL WORK

(76) Inventor: Suk Song Oh, 358-5 Sjikdong, Dukhoi APT 213 Ho, Hungdukgu, Chungjushi, Choongchungbukdo (KR), 361-102

( * ) Notice: Subject to any disclaimer, the term of this patent is extended or adjusted under 35 U.S.C. 154(b) by 27 days.

(21) Appl. No.: 10/279,233

(22) Filed: Oct. 25, 2002

(65) Prior Publication Data

US 2004/0009452 A1 Jan. 15, 2004

(30) Foreign Application Priority Data

Jul. 12, 2002 (KR) ........................................ 2002-40632

(51) Int. Cl.⁷ ................................................. A61G 5/02
(52) U.S. Cl. .............................. 433/81; 433/224; 433/32
(58) Field of Search ............................ 433/81, 83, 224, 433/102, 32

(56) References Cited

U.S. PATENT DOCUMENTS

| | | | |
|---|---|---|---|
| 4,265,618 A | 5/1981 | Herskovitz et al. | 433/32 |
| 4,357,136 A | 11/1982 | Herskovitz et al. | 433/224 |
| 4,392,827 A | 7/1983 | Martin | 433/32 |
| 4,441,013 A | 4/1984 | Masreliez | 219/231 |
| 4,527,560 A | 7/1985 | Masreliez | 128/303.1 |
| 4,992,045 A | 2/1991 | Beisel | 433/32 |
| 5,043,560 A | 8/1991 | Masreliez | 219/497 |
| 5,893,713 A | 4/1999 | Garman et al. | 433/32 |
| 5,921,775 A | 7/1999 | Buchanan | 433/102 |
| 5,934,903 A | 8/1999 | Marlin | 433/81 |
| 6,168,432 B1 | 1/2001 | Marlin | 433/81 |
| 6,270,343 B1 | 8/2001 | Martin | 433/32 |
| 6,701,189 B2 * | 3/2004 | Fang et al. | 607/48 |
| 2002/0086264 A1 * | 7/2002 | Okawa et al. | 433/89 |

FOREIGN PATENT DOCUMENTS

| | | |
|---|---|---|
| JP | 2002-143183 | 5/2002 |
| KR | 20020040632 | 1/2000 |

* cited by examiner

Primary Examiner—Pedro Philogene
Assistant Examiner—Candice C. Stokes
(74) Attorney, Agent, or Firm—Park & Sutton LLP; John K. Park

(57) ABSTRACT

A complex root canal plugging apparatus for dental work, with a gun-type injection device and a pen-type vertical spreader connected to a single controller, is disclosed. The spreader consists of a body part, a power transmission part, a chucking part, and a plugger tip. The power transmission part consists of a first contact ring connected to the first electric wire, an insulating ring, a second contact ring. The plugger tip consists of a hollow mounting part inserted into the chuck, a hollow heating part extending from the mounting part while being tapered, with a heating member installed in the end of the heating part. A second electric wire is connected to the second contact ring, and axially extends through the heating part after passing through the mounting part while coming into contact with the upper portion of the heating member.

8 Claims, 4 Drawing Sheets

[FIG.1]
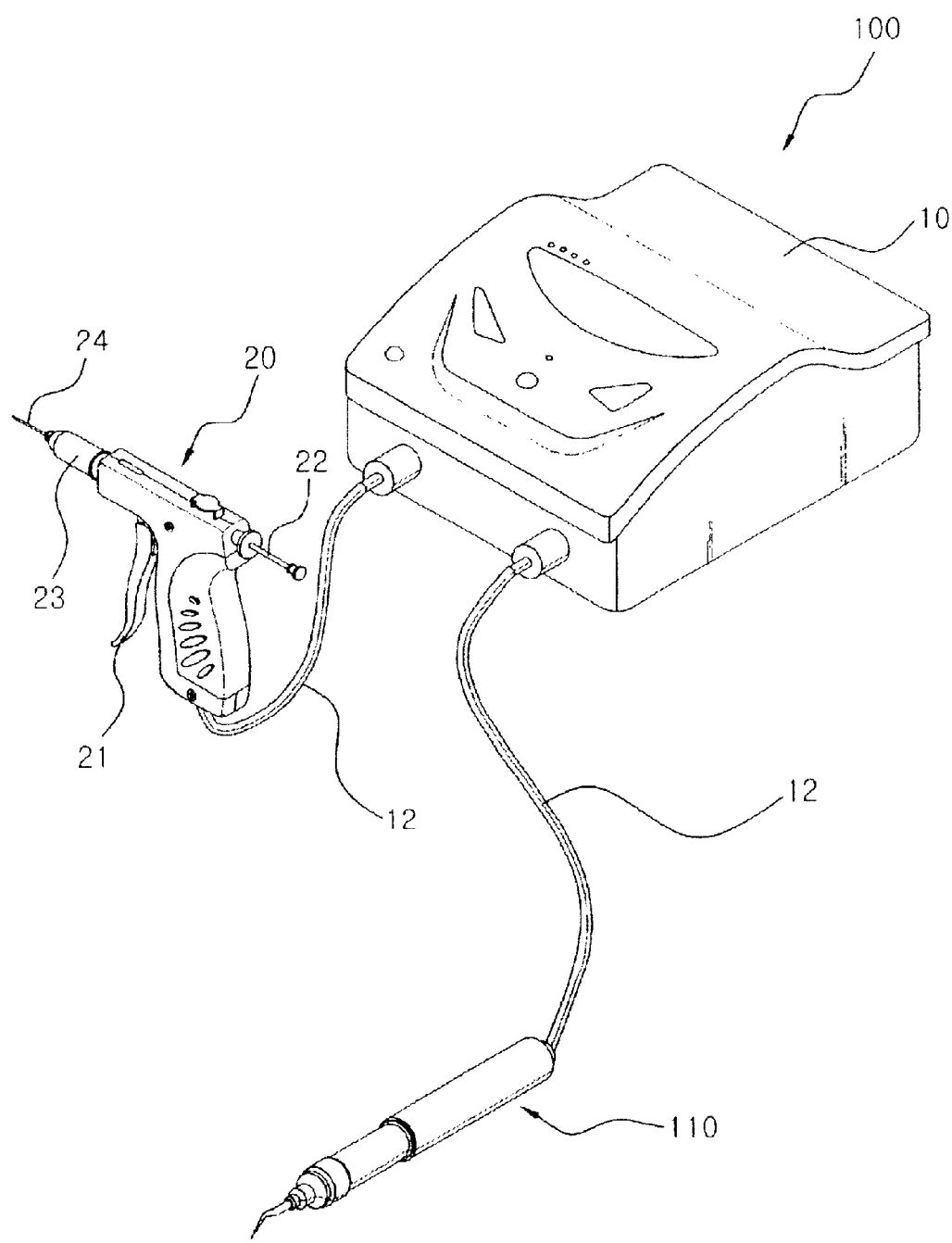

[FIG.2]
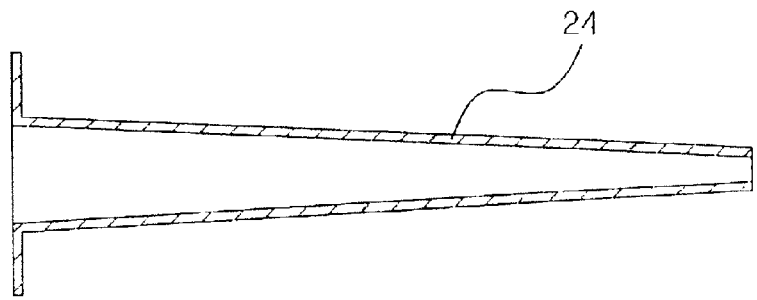
[FIG.3]
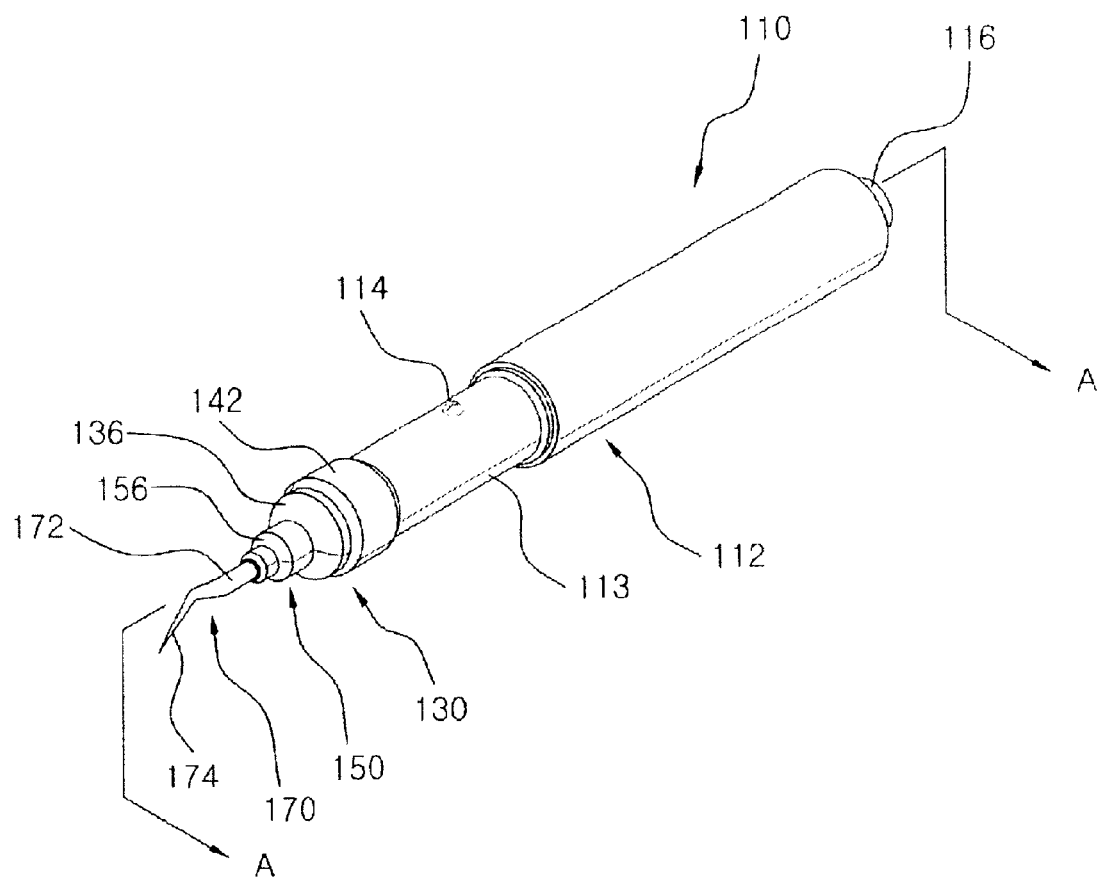

[FIG.4]
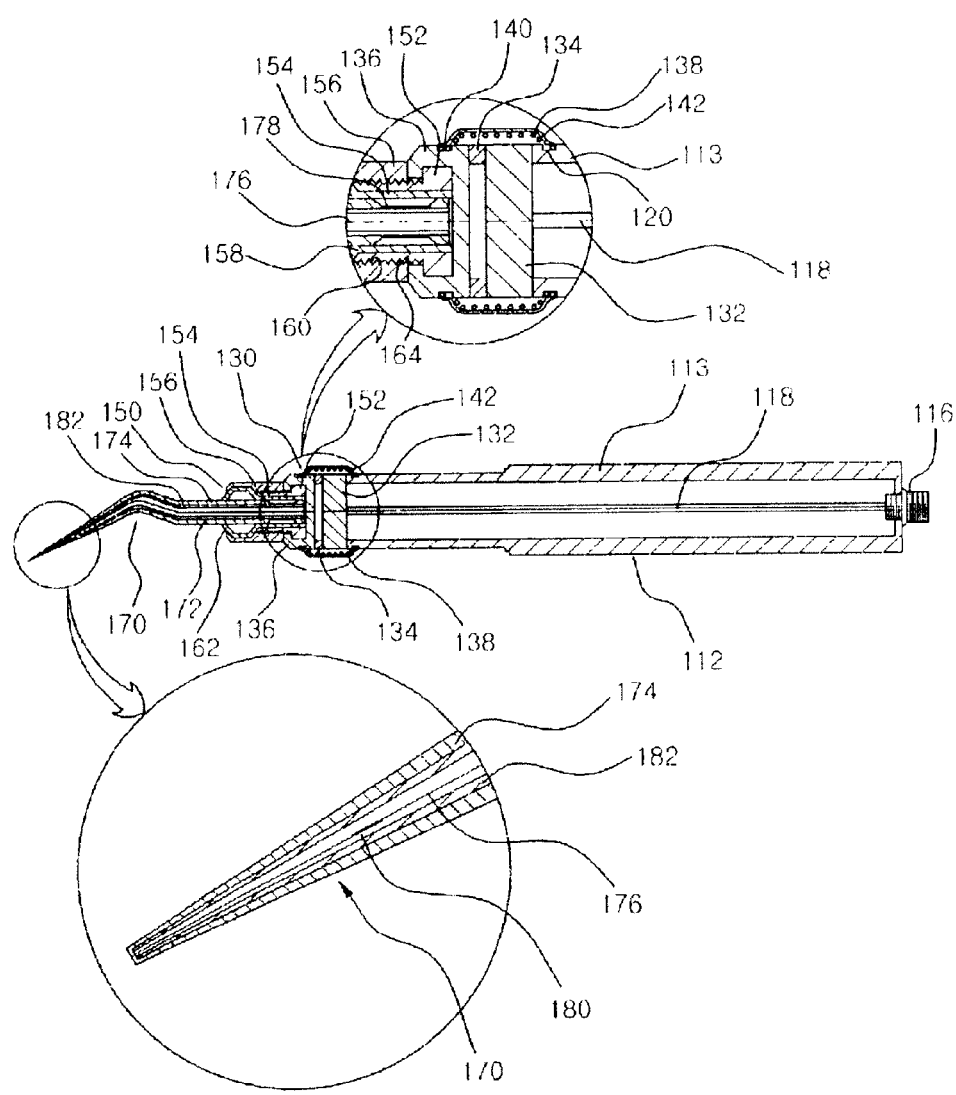

[FIG.5]
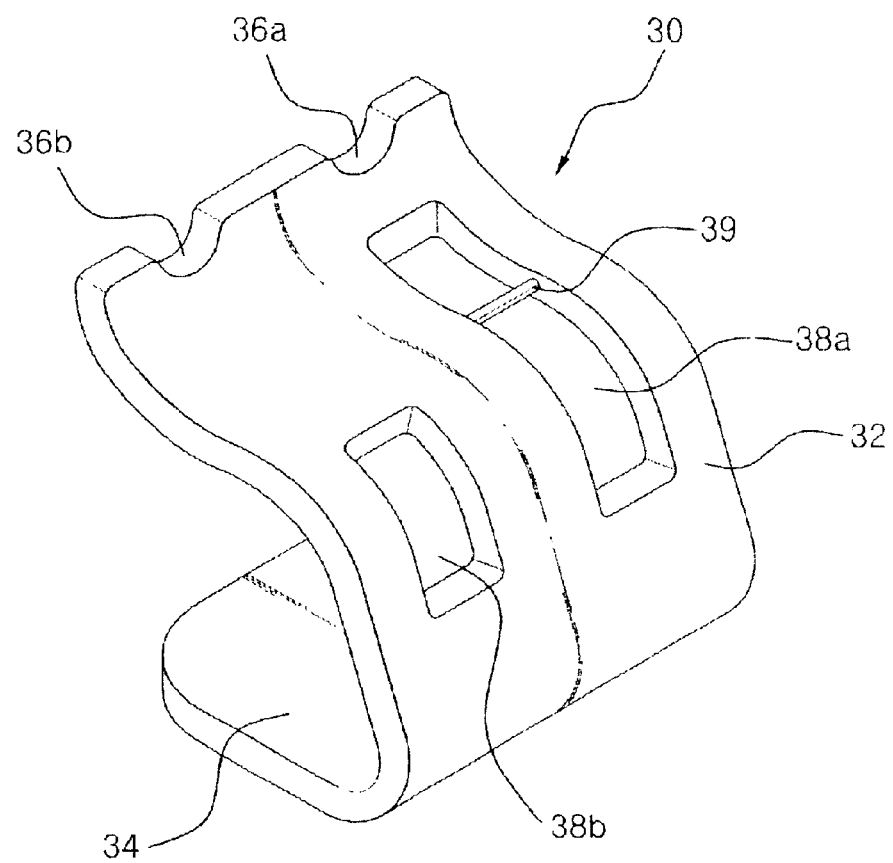

COMPLEX ROOT CANAL PLUGGING APPARATUS FOR DENTAL WORK

CLAIMING FOREIGN PRIORITY

The applicant claims and requests a foreign priority, through the Paris Convention for the Protection of Industry Property, based on a patent application filed in the Republic of Korea (South Korea) with the filing date of Jul. 12, 2002, with the application number 2000-0040632, by the applicant. (See the Attached Declaration)

BACKGROUND OF THE INVENTION

1. Field of the Invention

The present invention relates, in general, to a root canal plugging apparatus for dental work and, more particularly, to a complex root canal plugging apparatus consisting of a controller, a gun-type injection device, a pen-type vertical spreader, and a cradle for holding both the injection device and the spreader, thus allowing a dentist to more easily, rapidly and precisely pack a root canal with a filler material while performing a root canal plugging procedure during a nerve treatment in a dental clinic.

2. Description of the Prior Art

During a dental treatment for a decayed tooth in a dental clinic, a dentist appropriately removes decayed parts from the tooth using dental drills, reamers, files and burs, and performs a root canal plugging procedure for packing a root canal with a filler material, prior to covering the tooth packed with the filler material using a crown.

Typically, gutta-percha cones have been preferably used as such filler materials during the root canal plugging procedures. The gutta-percha is the milky juice of Malaysian trees of the sapodilla family, especially Palaguium or Payena trees, and has a semisolid phase at a normal temperature, but becomes a hard rubberlike gum when being compressed or heated. The gutta-percha in the form of such a hard rubberlike gum is so-called "white gutta-percha". The dentally usable gutta-percha cones are produced by adding zinc oxide, barium sulfate, wax and pigment to the gutta-percha, and kneading them in a mixer prior to extruding the mixture in the form of a sheet using a roll. The sheet type extruded mixture is, thereafter, cut into pieces, and the pieces are shaped into cones to form desired gutta-percha cones having different sizes. The gutta-percha cones have been most widely used as the root canal filler materials since they are biologically compatible with living bodies and not harmful to the root apexes of human teeth.

The recently marketed gutta-percha cones include standardized cones and accessory cones. The standardized gutta-percha cones have the same shapes as the dental files. During a nerve treatment procedure for a decayed tooth, infected nervous tissues are primarily removed from the root of the decayed tooth through rotating and cutting actions of a file, thus forming a conical root canal in the tooth. Thereafter, the root canal is plugged with a gutta-percha cone having the same size as the file so as to prevent the root of the tooth from being reinfected. In dentistry, the procedure for plugging the root canal with a gutta-percha cone is so-called "a root canal plugging procedure". In a conventional root canal plugging procedure, it is almost impossible to completely plug each root canal with one standardized gutta-percha cone, but five to eight cones are typically used for completely plugging the root canal since the root canal is not precisely formed during the procedure for forming the root canal using a file, and there remains a substantial gap between the standardized gutta-percha cone and the root canal wall. Such an inferior precision of the root canal is typically caused by unskillfulness of a dentist rather than inferior operational precision of the file.

When it is desired to plug a root canal having a size different from that of a file used in a procedure for forming the root canal, a standardized gutta-percha cone is primarily packed in the root canal until the cone reaches the root apex. Thereafter, the remaining empty portion in the root canal is secondarily packed with accessory cones using a spreader, thus completely plugging the root canal. However, such conventional procedures for plugging root canals with standardized and accessory gutta-percha cones consume much time, so it is very inconvenient to dentists and patients, in addition to giving pains to the patients. In addition, the conventional root canal plugging procedures using the standardized and accessory gutta-percha cones cannot completely plug an accessory canal with gutta-percha cones even though it is possible to plug a main canal with gutta-percha cones. Therefore, the root of a decayed tooth may be reinfected after treatment.

In the prior art, a variety of dental implements used in such root canal plugging procedures have been proposed. As examples, gun-type injection devices and pen-type spreaders, which are connected to separate controllers, have been proposed and used.

An example of such conventional dental implements for performing root canal plugging procedures is referred to U.S. Pat. No. 5,893,713, disclosing an apparatus consisting of an electric power control and a temperature controllable probe connected to the control. However, the apparatus disclosed in the above U.S. patent is problematic in that the resistance heater of the plugger element provided at the probe is too short in its length. Furthermore, the above U.S. patent does not disclose the material of the electric wire installed in the probe. When using a conventional electric wire in the probe, the wire causes a problem in that it provides an inferior electric conductivity in comparison with silver wires.

In addition, U.S. Pat. Nos. 5,934,903 and 6,168,432 each disclose a needle for filler material injection devices. However, the needles disclosed in the above U.S. patents are problematic in that it is very difficult to insert the needles into small-sized root canals. In addition, the hollow needles are not tapered, so they do not allow a smooth flowing of softened filler materials through them when inserting the filler materials into root canals, and, furthermore, the needles may be easily broken in root canals during root canal plugging procedures.

SUMMARY OF THE INVENTION

Accordingly, the present invention has been made keeping in mind the above problems occurring in the prior art, and an object of the present invention is to provide a complex root canal plugging apparatus for dental work, which consists of a controller, a gun-type injection device, a pen-type vertical spreader, and a cradle for holding both the injection device and the spreader, thus allowing a dentist to more easily, rapidly and precisely pack a root canal with a filler material while performing a root canal plugging procedure during a nerve treatment in a dental clinic.

In order to accomplish the above objects, the present invention provides a complex root canal plugging apparatus for dental work, comprising: a controller having a lithium-ion battery therein; a gun-type injection device electrically connected to the controller and used for inserting a filler material into a root canal while changing the phase of the filler material from a solid to a fluid phase, the gun-type injection device being provided with a trigger for triggering a discharge of the filler material from the injection device, a plunger at a first end thereof for compressing the filler material, and a filler material container at a second end thereof, with a needle installed at the container; and a pen-type vertical spreader electrically connected to the controller and used for enhancing the fluidity of the filler material previously inserted in the root canal by the injection device, thus allowing the filler material to be effectively packed into the root canal.

The plugging apparatus of this invention, having the gun-type injection device and the pen-type vertical spreader, also includes a cradle for holding both the injection device and the spreader, thus allowing a dentist to more easily, rapidly and precisely pack a root canal with a filler material while performing a root canal plugging procedure during a nerve treatment in a dental clinic.

BRIEF DESCRIPTION OF THE DRAWINGS

The above and other objects, features and other advantages of the present invention will be more clearly understood from the following detailed description taken in conjunction with the accompanying drawings, in which:

FIG. 1 is a front perspective view of a complex root canal plugging apparatus for dental work in accordance with the preferred embodiment of the present invention;

FIG. 2 is a sectional view of a needle installed at a gun-type injection device included in the root canal plugging apparatus of FIG. 1;

FIG. 3 is a perspective view of a pen-type vertical spreader included in the root canal plugging apparatus of FIG. 1;

FIG. 4 is a sectional view of the spreader taken along the line A—A of FIG. 3; and FIG. 5 is a perspective view of a cradle included in the root canal plugging apparatus of FIG. 1.

DETAILED DESCRIPTION OF THE INVENTION

Reference should now be made to the drawings, in which the same reference numerals are used throughout the different drawings to designate the same or similar components.

FIG. 1 is a front perspective view of a complex root canal plugging apparatus for dental work in accordance with the preferred embodiment of the present invention.

As shown in the drawing, the complex root canal plugging apparatus 100 according to the invention comprises a controller 10, a gun-type injection device 20, and a pen-type vertical spreader 110. The controller 10 applies electric power to both the injection device 20 and the spreader 110, and controls their operations during a root canal plugging procedure. The gun-type injection device 20 is electrically connected to the controller 10 and used for inserting a filler material into a root canal while changing the phase of the filler material from a solid to a fluid phase. The pen-type vertical spreader 110 is electrically connected to the controller 10 and used for enhancing the fluidity of the filler material previously inserted in the root canal by the injection device 20. The plugging apparatus 100 of this invention also has a cradle 30 for holding both the injection device 20 and the spreader 110.

The injection device 20 has a shape similar to that of a conventional gun, with a trigger 21 provided at the lower portion of the injection device 20 for triggering a discharge of the softened filler material from the injection device 20. This injection device 20 also has a plunger 22 at a first end thereof for compressing the filler material, and a filler material container 23 at a second end thereof, with a needle 24 installed at the end of the container 23 as shown in FIG. 2. The needle 24 consists of a hollow body that is tapered in a direction from the container 23 to its free end such that the inner diameter of the hollow needle 24 is gradually reduced along the same direction. The tapered needle 24 allows a smooth flowing of softened filler material through it. In the present invention, the above needle 24 is preferably made of an alloy of 90~95% silver and 5~10% another metal selected from the group consisting of iron (Fe), cobalt (Co), zinc (Zn), palladium (Pd), and titanium (Ti). The longitudinal cross-section of the needle 24 is shown in FIG. 2.

In the apparatus 100 of this invention, a lithium-ion battery is preferably used as a battery installed in the controller 10, so it is possible to reduce the time for charging the controller 10 with electric power and increase the using time of the controller 10 after every charging, and remarkably reduce the weight of the controller 10.

FIG. 3 is a perspective view of the pen-type vertical spreader included in the root canal plugging apparatus of FIG. 1. FIG. 4 is a sectional view of the spreader taken along the line A—A of FIG. 3.

As shown in the drawings, the pen-type vertical spreader 110 comprises a body part 112, a power transmission part 130, a chucking part 150, and a plugger tip 170.

In a detailed description of the spreader 110, the body part 112 consists of a body 113, a connector 116 and a first electric wire 118. The body 113 has a hollow cylindrical shape, with a display lamp 114 exteriorly mounted on the circumferential surface of the body 113 for displaying a power-on condition of the spreader 110. The connector 116 is mounted at a first end of the body 113 and connected to a cord 12 extending from the controller 10. The first electric wire 118 is connected to the connector 116 at a first end thereof, and axially extends in the interior of the hollow body 113 to reach a second end of the body 113. In the present invention, the first electric wire 118 is preferably made of silver (Ag) having excellent electric conductivity. A first annular seating groove 120 is externally formed around the circumferential surface of the body 113 at a position adjacent to the second end of the body 113. Installed at the second end of the body 113 are the power transmission part 130 and the chucking part 150, with the plugger tip 170 installed at the chucking part 150 through a fitting method.

The power transmission part 130 comprises a first contact ring 132, an insulating ring 134, a second contact ring 136, and an annular spring switch 138. The first contact ring 132 is preferably made of brass to form an annular shape. This first contact ring 132 is closely mounted to the second end of the body 113, and connected to the second end of the first electric wire 118. In addition, the second contact ring 136, preferably made of brass in the same manner as that of the first contact ring 132, is closely positioned outside the first contact ring 132, with the insulating ring 134 made from acetal and closely interposed between the two contact rings 132 and 136. A second annular seating groove 140 is externally formed around the circumferential surface of the second contact ring 136 so as to correspond to the first seating groove 120. In such a case, the second seating groove 140 has the same shape as that of the first seating groove 120. The spring switch 128, having an annular shape, is fitted over the spreader 110 such that it partially covers both the body part 112 and the power transmission part 130. In such a case, the edges of both ends of the switch 128 are seated in the first and second seating grooves 120 and 140, respectively, in a way such that the switch 128 does not come into direct contact with the circumferential surfaces of the first and second contact rings 132 and 136. The outer circumferential surface of the spring switch 128 is covered with a silicone tube 142.

The chucking part 150 consists of a locking flange 152, a chuck 154 and a chuck nut 156. The locking flange 152 is set in the interior of the second contact ring 136 such that the outer circumferential surface of the flange 152 comes into contact with the inner circumferential surface of the second contact ring 136. In such a case, a cylindrically locking boss 158 axially extends from an end surface of the flange 152 such that it projects from the second contact ring 136 to the outside. The circumferential surface of the locking boss 158 is externally threaded to form external threads 160 thereon. The chuck 154 with a plurality of claws 162 is fitted into the locking flange 152 after passing through the boss 158. The chuck nut 156 is externally tightened to the locking boss 158 of the flange 152 so as to cover the chuck 154 while compressing the claws 162. The chuck nut 156 is internally threaded to form internal threads 164, so the internal threads 164 engage with the external threads 160 of the locking boss 158 when tightening the nut 156 to the boss 158.

The plugger tip 170 consists of a mounting part 172, a heating part 174, and a second electric wire 176. The mounting part 172 of the plugger tip 170 has a hollow cylindrical shape, and is inserted into the chuck 154. In such a case, in order to prevent an undesired rotation of the mounting part 172 in the chuck 154, a rectangular groove 178 is formed at a predetermined position on the circumferential surface of the mounting part 172. The heating part 174 has a hollow cylindrical shape in the same manner as that described for the mounting part 172. This hollow cylindrical heating part 174 extends from the end of the hollow cylindrical mounting part 172 while being bent downward and tapered in a direction from the end of the mounting part 172 to the free end of the heating part 172. Therefore, the inner diameter of the heating part 174 is gradually reduced in the same direction. Installed in the free end of the heating part 174 is a heating member 180. The heating member 180 is preferably made of an alloy of copper and nickel, and installed in the end of the heating part 174 such that one end of the heating member 180 projects from the end of the heating part 174 and the other end is set in the end of said heating part 174. The second electric wire 176, made of silver (Ag) in the same manner as that described for the first electric wire 118, is connected to the second contact ring 136 and axially extends through the heating part 174 after passing through the mounting part 172, and comes into close contact with the upper portion of the heating member 180. In the mounting part 172 and the heating part 174, the second electric wire 176 is covered with a capton tube 182. When an electric current is applied to the second wire 176, heat is generated from the heating part 174 due to a difference in resistance between the second wire 176 and the heating member 180. In the present invention, it is possible to produce plugger tips 170 having various sizes and design the tips 170 such that the tips 170 are controllable in the flow of electric current through them.

In the present invention, it is preferable to produce the heating part 174 using a nickel-titanium-silver alloy, which is prepared by adding 0.1~10% silver to 90~99.9% nickel-titanium alloy and has excellent corrosion resistance and excellent biological compatibility with living bodies.

The gun-type injection device 20 and the pen-type vertical spreader 110 are held on the cradle 30, which allows a dentist to easily and conveniently use the injection device 20 and the spreader 110 within a limited space during a root canal plugging procedure. As shown in FIG. 5, the cradle 30 has a single structure consisting of a cradle plate part 32 having an S-shaped cross-section, and a support plate part 34 integrally and horizontally extending from the lower end of the cradle plate part 32 and stably supporting the cradle 30 on a support surface. First and second holding notches 36a and 36b are formed along the top edge of the cradle plate part 32, while first and second holding openings 38a and 38b are formed on the cradle plate part 32 at positions under the first and second holding notches 36a and 36b, respectively. In the cradle 30, a horizontal bar 39 extends between opposite edges of the first holding opening 38a at a predetermined position for holding the trigger 21 of the gun-type injection device 20.

The operation and effect of the complex root canal plugging apparatus 100 of this invention will be described herein below.

In order to treat a decayed tooth, a dentist appropriately cuts the tooth using an appropriate dental file (not shown) to form a root canal, and selects a gutta-percha cone having a size similar to that of the file prior to inserting the cone into the root canal. After inserting the gutta-percha cone into the root canal, the dentist prepares the pen-type vertical spreader 110. In order to prepare the spreader 110, the dentist loosens the chuck nut 156 from the locking boss 158 to release the compressed claws 162 of the chuck 154, and inserts the mounting part 172 of the plugger tip 170 into the chuck 154. Thereafter, the second electric wire 176 projecting from the end of the mounting part 172 is carefully manipulated to come into close contact with the second contact ring 136, prior to fully tightening the chuck nut 156 to the locking boss 158. When the nut 156 is tightened to the boss 158 as described above, the claws 162 of the chuck 154 are compressed to prevent an undesired removal of the mounting part 172 from the chuck 154.

After mounting the plugger tip 170 to the spreader 110, the cord 12 extending from the controller 10 is connected to the connector 116 of the body 113 of the spreader 110. When the controller 10 is turned on after the preparation of the spreader 110, an electric current flows through both the first electric wire 118 and the first contact ring 132. When the dentist, gripping the body 113 of the spreader 110 with one hand, operates the spring switch 138 by finger-pressing the switch 138, the switch 138 electrically couples the second contact ring 136 to the first contact ring 132, thus causing an electric current to flow from the first contact ring 132 to the second contact ring 136. Therefore, the second contact ring 136 applies an electric current to the second wire 176 connected to the ring 136, thus so the current flows through the wire 176. When the electric current is applied to the second wire 176, heat is generated from the heating part 174 due to a difference in resistance between the end of the second wire 176 and the heating member 180. When the heating part 174 generates heat as described above, it transmits the heat to the previously inserted gutta-percha cone. In such a case, the heat from the heating part 174 is transmitted to a position spaced from the root apex in the root canal by a distance of 3~5 mm, thus softening the gutta-percha cone and effectively plugging the root canal with the softened gutta-percha cone. The dentist removes a surplus part of the softened gutta-percha cone from the upper part of the root canal using the spreader 110. After plugging the root canal with the gutta-percha cone using the spreader 110, the dentist inserts the needle 24 of the gun-type injection device 20 into the root canal, and plugs the empty part of the root canal with a filler material, thus finishing a root canal plugging procedure. The pen-type spreader 110 of this invention may be preferably used in procedures for plugging tooth cavities with sealants, in addition to the root canal plugging procedures.

As described above, the complex root canal plugging apparatus 100 for dental work of this invention is designed such that both a gun-type injection device 20 and a pen-type vertical spreader 110 are connected to a single controller 10 at the same time. Therefore, the injection device 20 and the spreader 110 are used with the single controller 10, so the apparatus 100 allows a dentist to more easily, quickly and precisely pack a root canal with a filler material while performing a root canal plugging procedure during a nerve treatment in a dental clinic.

The heating part 174 of the pen-type spreader 110 is designed such that it is tapered. Such a tapered heating part 174 of the spreader 110 is easily inserted into a root canal, and allows a smooth flowing of softened filler material in the root canal. In addition, the first and second electric wires 118 and 176 provided in the spreader 110 are made from silver having excellent electric conductivity as described above, so the spreader 110 is advantageous in that it more quickly generates heat, in comparison with conventional spreaders.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A complex root canal plugging apparatus for dental work, comprising:

a controller having a lithium-ion battery therein;

a gun-type injection device electrically connected to said controller and used for inserting a filler material into a root canal while changing a phase of the filler material from solid to a fluid phase, said gun-type injection device being provided with a trigger for triggering a discharge of the filler material from the injection device, a plunger at a first end thereof for compressing the filler material, and a filler material container at a second end thereof, with a needle installed at the container; and a pen-type vertical spreader electrically connected to said controller and used for enhancing fluidity of the filler material previously inserted in the root canal by the injection device, thus allowing the filler material to be effectively packed into the root canal, wherein said pen-type vertical spreader comprises:

a body part consisting of:

a body having hollow cylindrical shape, with a first annular seating groove externally formed around a circumferential surface of said body at a position adjacent to a second end of the body;

a connector mounted at a first end of said body and connected to a cord extending from said controller; and a first electric wire connected to the connector at a first end thereof, and axially extending in the interior of said body to reach the second end of the body at a second end thereof;

a power transmission part consisting of:

a first contacting ring mounted to the second end of said body and connected to the second end of said first electric wire;

an insulating ring positioned outside the first contact ring;

a second contact positioned outside the insulating ring such than said insulating ring is closely interposed between the first and second contact rings, with a second annular seating groove externally formed around a circumferential surface of the second contact ring so as to correspond a the first annular seating groove; and a spring switch fitted over the spreader while being seated in the first and second annular seating grooves at both ends thereof, respectively, said spring switch selectively and electrically coupling the first and second contact rings to each other;

a chucking par consisting of:

a locking flange set in the interior of said second contact ring, with a locking boss axially extending from an end surface of said locking flange such that the boss projects from he second contact ring to the outside;

a chuck fitted into said locking flange after passing through the boss; and a chuck nut rightened to said locking boss so as to selectively lock said chuck; and a plugger tip consisting of:

a mounting part having a hollow cylindrical shape, and being inserted into said chuck;

a heating part having a hollow cylindrical shape and extending from an end of said hollow cylindrical mounting part hue being bent downward and tapered in a direction from the end of the mounting part to a free end of the heating part, with a seating member installed in the free en of said heating part; and a second electric wire connected to said second contact ring, and axially extending through said heating part after passing through the mounting part while coming into contact with a upper portion of said heating member.

2. The complex root canal plugging apparatus according to claim 1, wherein a display lamp is exteriorly mounted on the circumferential surface of said body of the body part for displaying a power-on condition of said spreader.

3. The complex root canal plugging apparatus according to claim 1, wherein said locking boss has external threads on an outer circumferential surface thereof, said chuck has a plurality of claws, and said chuck nut has internal threads on an inner circumferential surface thereof, whereby the chuck nut compresses the claws to lock the chuck when the chuck nut is tightened to the locking boss.

4. The complex root canal plugging apparatus according to claim 1, wherein a rectangular groove is formed at a predetermined position on the circumferential surface of said mounting part so as to prevent an undesired rotation of said mounting part in the chuck.

5. The complex root canal plugging apparatus according to claim 1, wherein said heating part is made of a nickel-titanium-silver alloy, prepared by adding 0.1~10% silver to 90~99.9% nickel-titanic alloy, thus having excellent corrosion resistance and excellent biological compatibility with living bodies.

6. The complex root canal plugging apparatus according to claim 1, wherein said heating member is made of an alloy of copper and nickel, and installed in the end of said heating part such that a first end of the heating member projects from the end of the heating part and a second end of the heating member is set in the end of said heating part.

7. The complex root canal plugging apparatus according to claim 1, wherein a capton tube is arranged in both the mounting part and the heating part, and covers the second electric wire.

8. The complex rool canal plugging apparatus according to claim 1, wherein each of the first and second electric wires is made of silver having high electric conductivity.

* * * * *